United States Patent [19]

Kidani et al.

[11] Patent Number: 4,567,285

[45] Date of Patent: Jan. 28, 1986

[54] COMPLEX COMPOUNDS OF PLATINUM

[75] Inventors: Yoshinori Kidani; Masahide Noji, both of Nagoya, Japan

[73] Assignee: Yoshinori Kidani, Nagoya, Japan

[21] Appl. No.: 753,537

[22] Filed: Jul. 10, 1985

[51] Int. Cl.$^4$ ............................................. C07F 15/00
[52] U.S. Cl. .................................... 556/137; 548/301; 514/492
[58] Field of Search .......................... 556/137; 548/301

[56] References Cited

U.S. PATENT DOCUMENTS

| | | | |
|---|---|---|---|
| 4,137,248 | 1/1979 | Gale et al. | 556/137 |
| 4,169,846 | 10/1979 | Kidani et al. | 556/137 |
| 4,200,583 | 4/1980 | Kidani et al. | 556/137 |
| 4,255,347 | 3/1981 | Kidani et al. | 556/137 |
| 4,256,652 | 3/1981 | Kidani et al. | 556/137 |
| 4,410,544 | 10/1983 | Berg et al. | 556/137 |
| 4,477,387 | 10/1984 | Kidani et al. | 556/137 |

OTHER PUBLICATIONS

Gale et al., "Perliminary Studies of 4-Carboxyphthalato(1,2-Diaminocyclohexane) Platinum(II) . . . ", J. Clin. Hematol. Oncol., 9 (No. 3), 217 (1979).

Speer et al., "Preclinical Evaluation of Bis(Pyruvato)1-,2-Diaminocyclohexane Platinum(II) as a Potential Antitumor Agent," J. Clin. Hematol. Oncol., 13 (No. 4), 89 (1983).

Speer et al., "Antitumor Activity of Platinum Complexes of 1,2-Diaminocyclohexane Isomers," J. Clin. Hematol. Oncol., 8 (No. 2), 44 (1978).

*Primary Examiner*—Helen M. S. Sneed

*Attorney, Agent, or Firm*—Cushman, Darby & Cushman

[57] ABSTRACT

Disclosed herein are novel complex compounds of platinum showing an antitumor activity, represented by the formula(I):

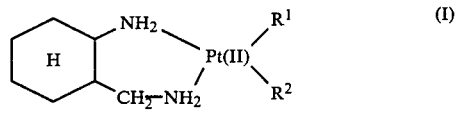

wherein one of $R^1$ and $R^2$ represents a group selected from the group consisting of (1) glucuronato groups whose hydroxyl groups may be acylated, (2) gluconato groups whose hydroxyl groups may be acylated, (3) pyruvato group and (4) nitrato group, and the other of $R^1$ and $R^2$ represents a group selected from the group consisting of (i) glucuronato groups whose hydroxyl groups may be acylated, (ii) gluconato groups whose hydroxyl groups may be acylated, (iii) pyruvato group and (iv) halogen atoms, or $R^1$ and $R^2$ represent together the group represented by the formula(II):

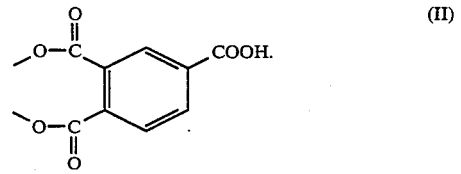

7 Claims, 18 Drawing Figures

COMPLEX COMPOUNDS OF PLATINUM

BACKGROUND OF THE INVENTION

The present invention relates to novel complex compounds of platinum, and more in detail, relates to novel complex compounds of platinum represented by the formula(I):

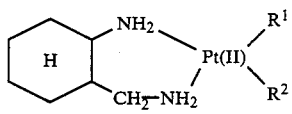

wherein one of $R^1$ and $R^2$ represents a group selected from the group consisting of (1) glucuronato groups whose hydroxyl groups may be acylated, (2) gluconato groups whose hydroxyl groups may be acylated, (3) pyruvato group and (4) nitrato group, and the other of $R^1$ and $R^2$ represents a group selected from the group consisting of (i) glucuronato groups whose hydroxyl groups may be acylated, (ii) gluconato groups whose hydroxyl groups may be acylated, (iii) pyruvato group and (iv) halogen atoms, or $R^1$ and $R^2$ represent together the group represented by the formula(II):

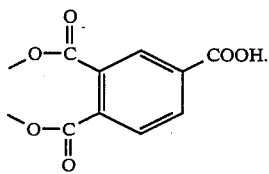

The compounds represented by the formula(I) have an anti-tumour activity and are useful compounds as an active ingredient of an anti-tumour agent.

Hitherto, it has been known that a certain kind of complex compounds of platinum has an anti-tumour activity.

As a result of producing novel complex compounds of platinum and examining the anti-tumour activity thereof, the present inventors have found that the compounds represented by the formula(I) have excellent anti-tumour activity, and the present invention has been attained on the basis of the present inventors' finding.

SUMMARY OF THE INVENTION

In an aspect of the present invention, there is provided complex compounds represented by the formula(I):

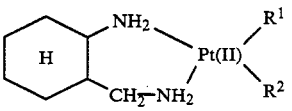

wherein one of $R^1$ and $R^2$ represents a group selected from the group consisting of (1) glucuronato groups whose hydroxyl groups may be acylated, (2) gluconato groups whose hydroxyl groups may be acylated, (3) pyruvato group and (4) nitrato group, and the other of $R^1$ and $R^2$ represents a group selected from the group consisting of (i) glucuronato groups whose hydroxyl groups may be acylated, (ii) gluconato groups whose hydroxyl groups may be acylated, (iii) pyruvato group and (iv) halogen atoms, or $R^1$ and $R^2$ represent together the group represented by the formula(II):

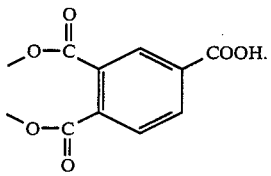

BRIEF EXPLANATION OF DRAWINGS

Of the attached drawings.

DETAILED DESCRIPTION OF THE INVENTION

The glucuronato group in $R^1$ and $R^2$ of the formula(I) is represented by the formula:

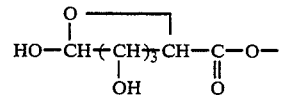

and the gluconato group in $R^1$ and $R^2$ of the formula(I) is represented by the formula:

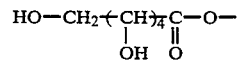

Of the hydroxyl groups of the above-mentioned glucuronato group and gluconato group in one of $R^1$ and $R^2$, preferably at least one may be acylated, and as the acyl group, for instance, acetyl group may be mentioned. It is preferable that four to five hydroxyl groups are acylated.

As the halogen atom in $R^1$ and $R^2$, chlorine atom, bromine atom, etc. may be mentioned.

Since 2-aminomethyl-cyclohexylamine (hereinafter referred to as AMCHA) which is used in the present invention as a raw material has two stereoisomers, the compounds represented by the formula(I) includes both the cis-isomer and the trans-isomer. Furthermore, since AMCHA has an asymmetric carbon, each of the compounds represented by the formula(I) includes not only the racemate but also both the d-isomer and the l-isomer.

Of the complex compounds of platinum according to the present invention (hereinafter referred to as the present compounds), the compounds in which $R^1$ or $R^2$ is not a halogen atom may be obtained by reacting one of various carboxylic acids or a salt thereof with [Pt(II)(NO$_3$)$_2$(AMCHA)] or [Pt(II) (SO$_4$) (AMCHA)] at a temperature of around 0° to 40° C. for 10 min to 4 weeks. In such a case of using about 1 mol of a monobasic carboxylic acid to 1 mol of the above-mentioned complex compound, the mono-substituted complex compound wherein one (NO$_3$) has been substituted by one molecule of the carboxylic acid is obtained, and in the case of using about 2 mols of the monobasic carboxylic acid, the di-substituted complex compound is obtained. In addition, in the case of using 1 mol of phthalic acid as the carboxylic acid to 1 mol of the above-mentioned complex compound, the di-substituted complex compound wherein two (NO₃) have been substituted by one molecule of phthalic acid is obtained.

As the carboxylic acid or the salt thereof, for instance, glucuronic acid, tetra-O-acetyl-α- or -β-glucuronic acid, gluconic acid, 2,3,4,6-tetra-O-acetylgluconic acid, penta-O-acetylgluconic acid, 4-carboxyphthalic acid, pyruvic acid, sodium salts thereof, potassium salts thereof and barium salts thereof may be mentioned.

Of the present compounds, the compound in which $R^1$ or $R^2$ is a halogen atom is obtained by reacting an amount of, preferably, 0.8 to 1.2 mol of an alkali halide with 1 mol of the complex compound, [Pt(II)(glucuronate)₂(AMCHA)] obtained as above, at a temperature around 0° to 10° C. for 10 to 40 hours.

As the alkali halide used as above, for instance, sodium chloride, potassium chloride and the like may be mentioned.

Figure 1:
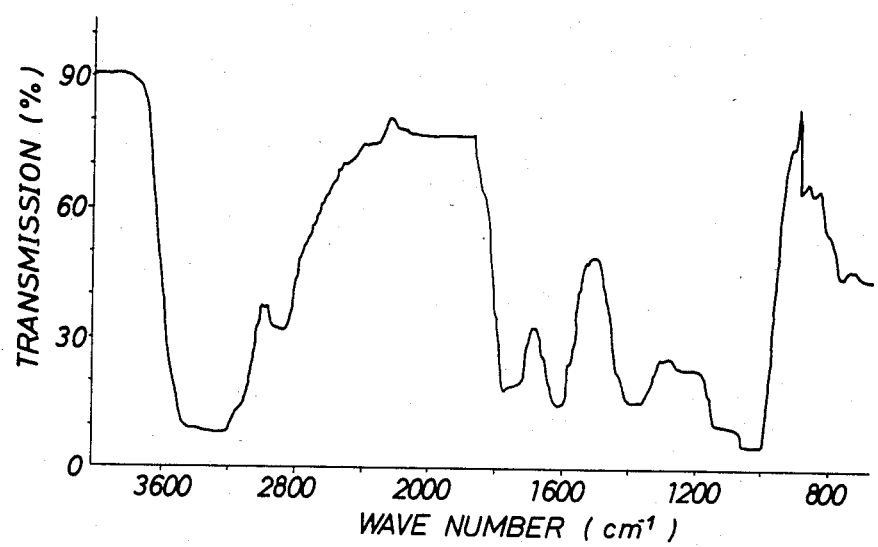
FIGS. 1 to 17 are the infrared absorption spectra of the present compounds Nos. 1 to 17, respectively.
Figure 2:
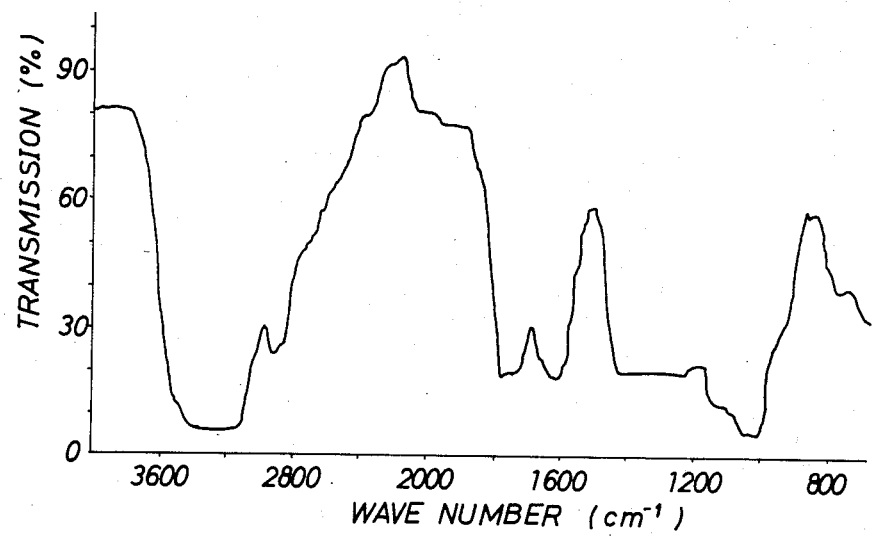
Figure 3:
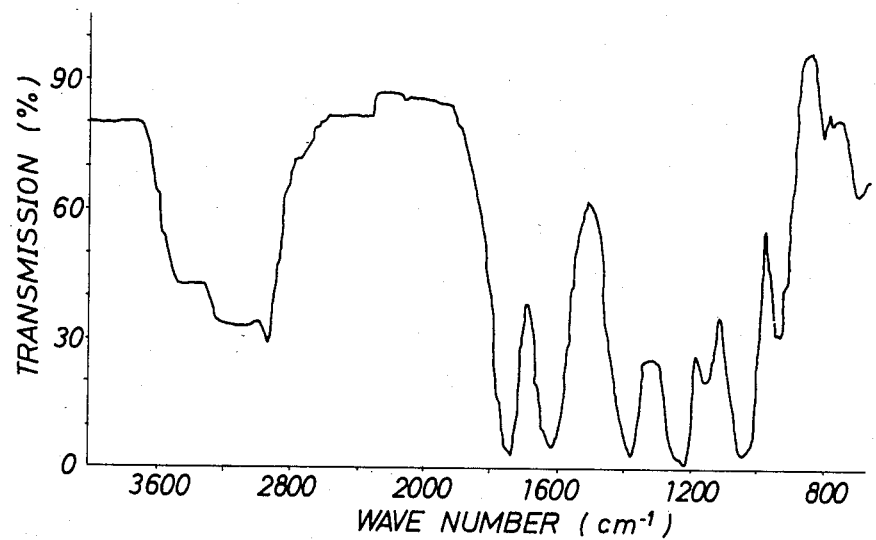
Figure 4:
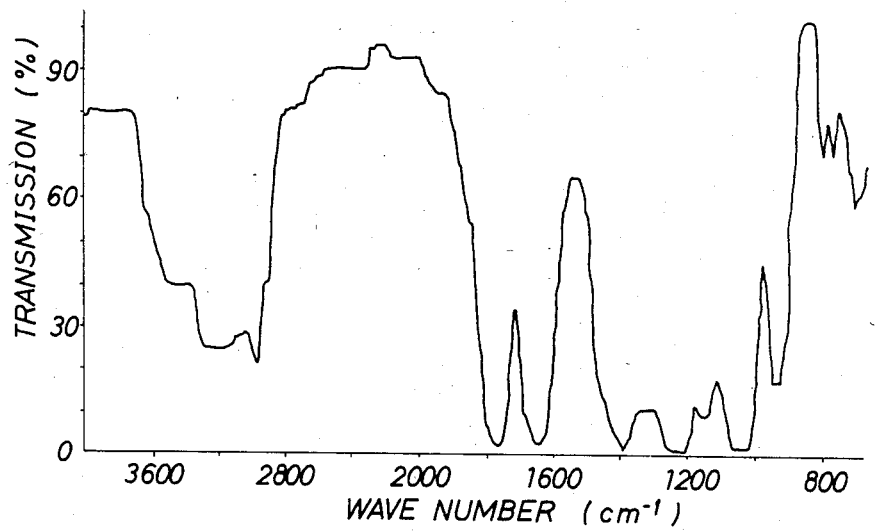
Figure 5:
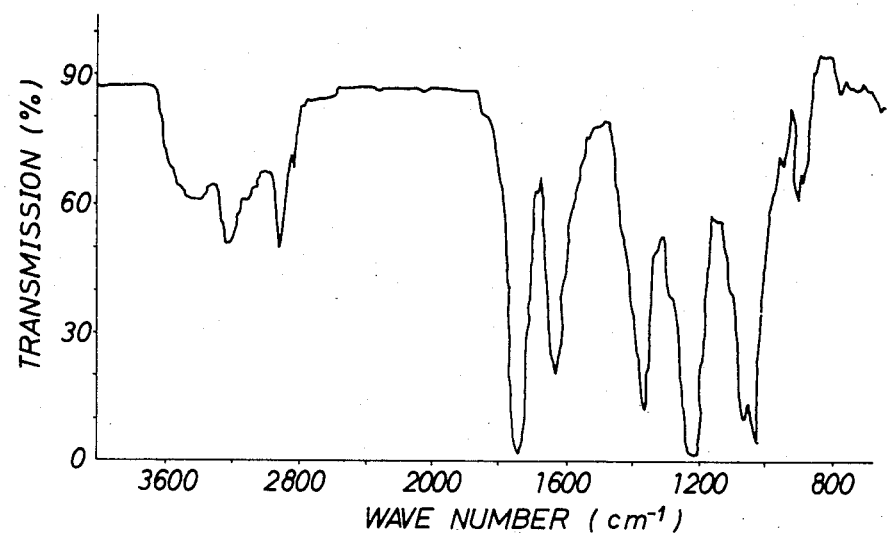
Figure 6:
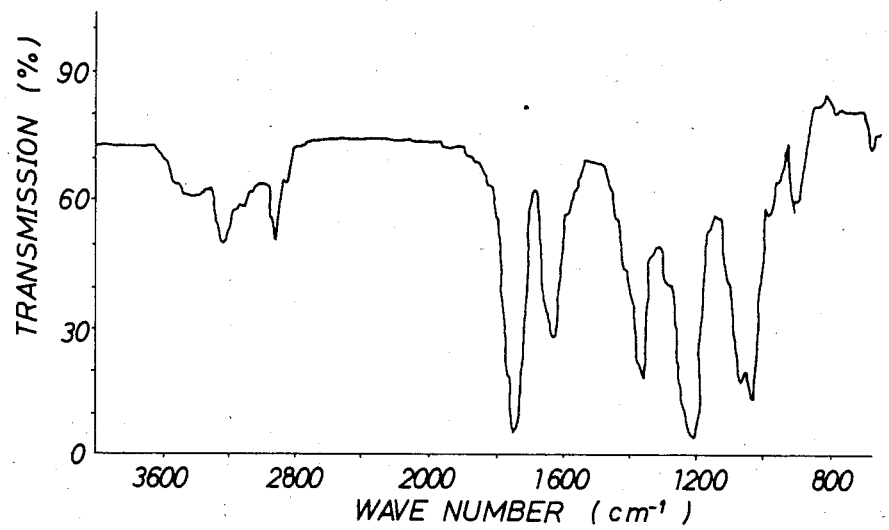
Figure 7:
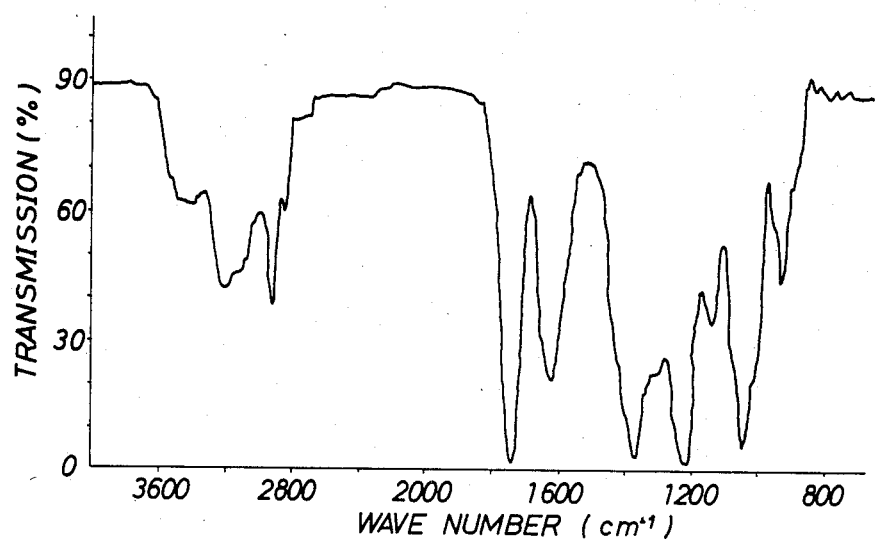
Figure 8:
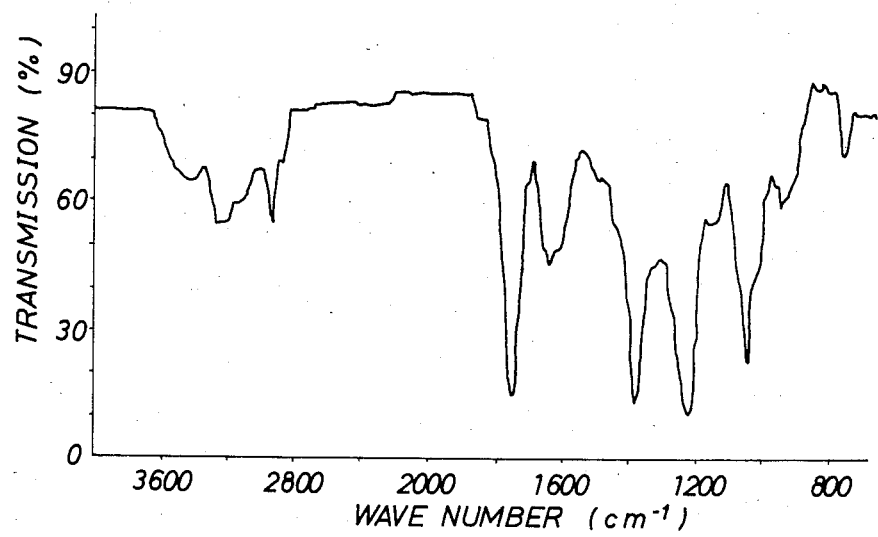
Figure 9:
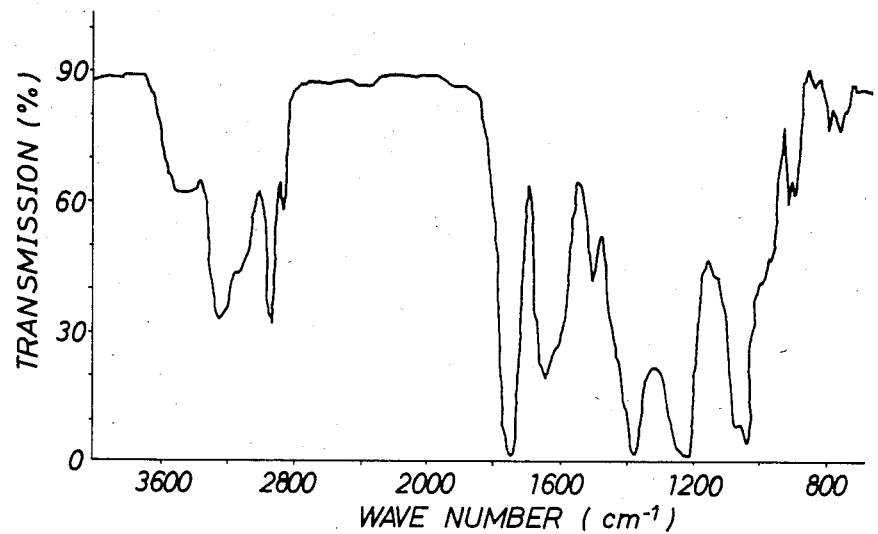
Figure 10:
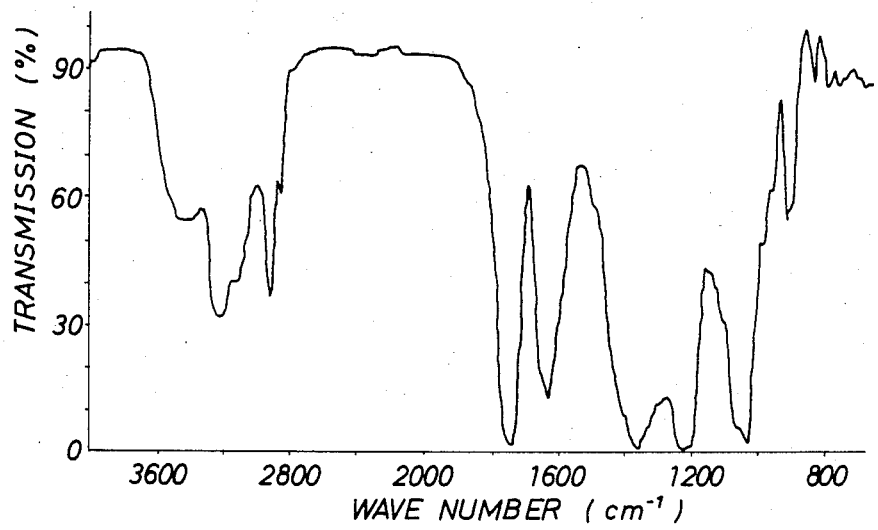
Figure 11:
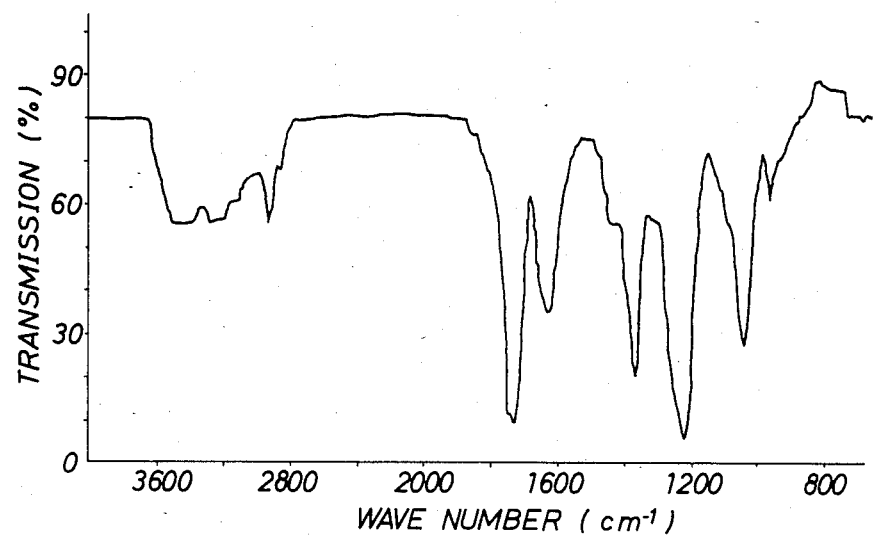
Figure 12:
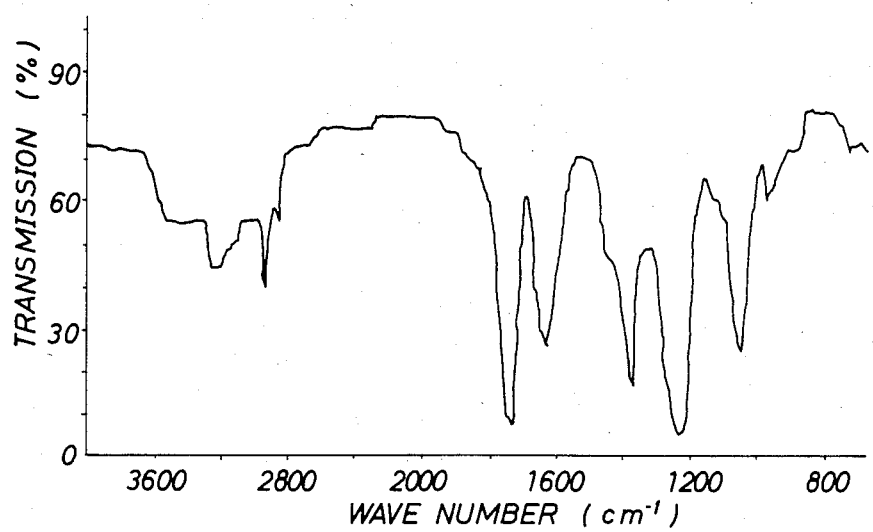
Figure 13:
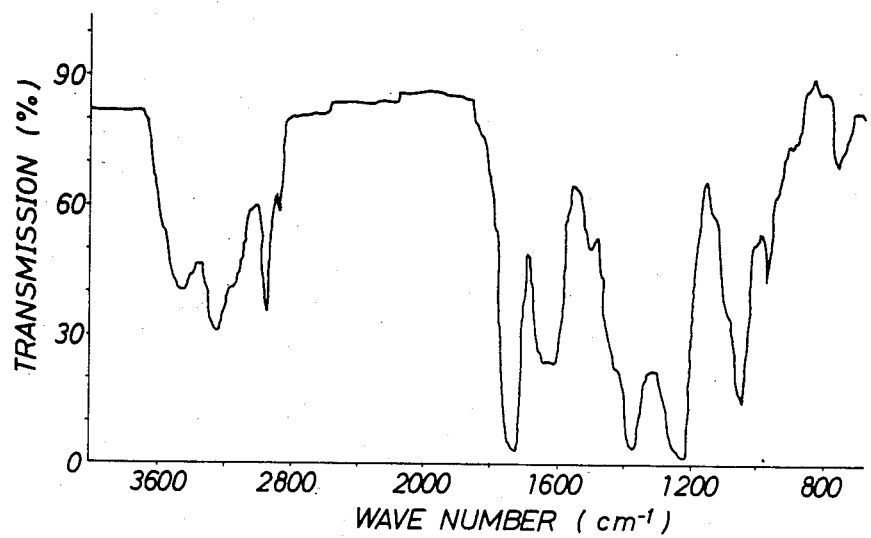
Figure 14:
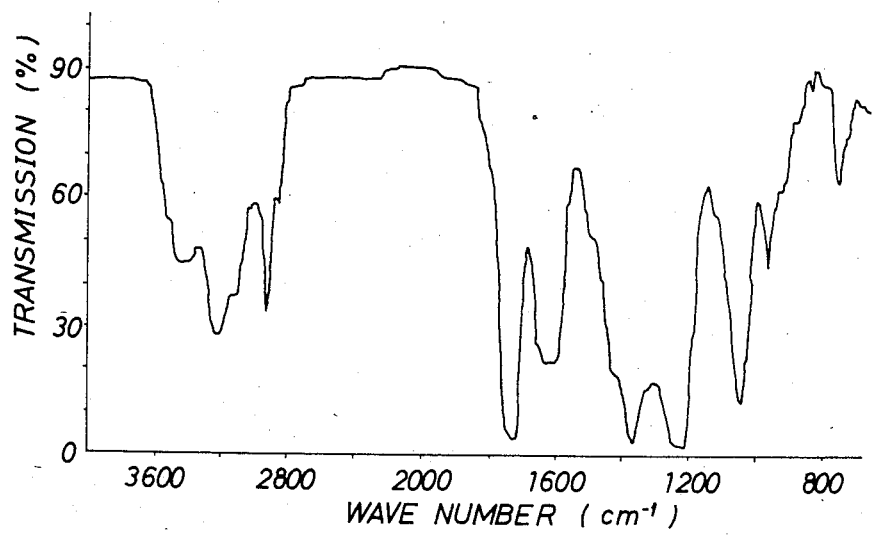
Figure 15:
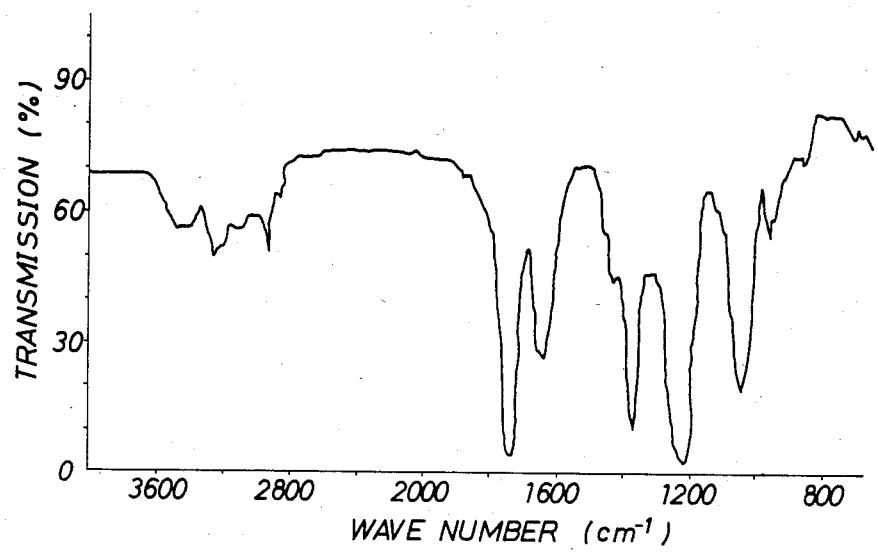
Figure 16:
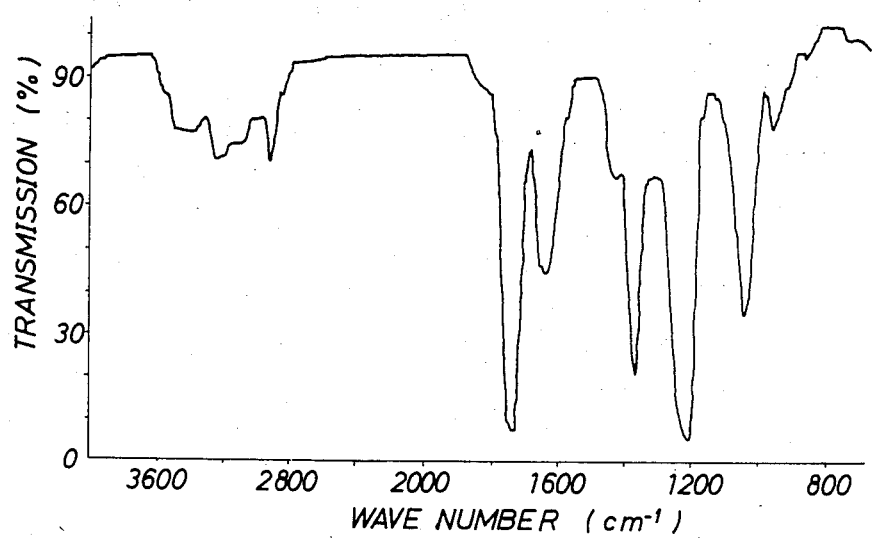
Figure 17:
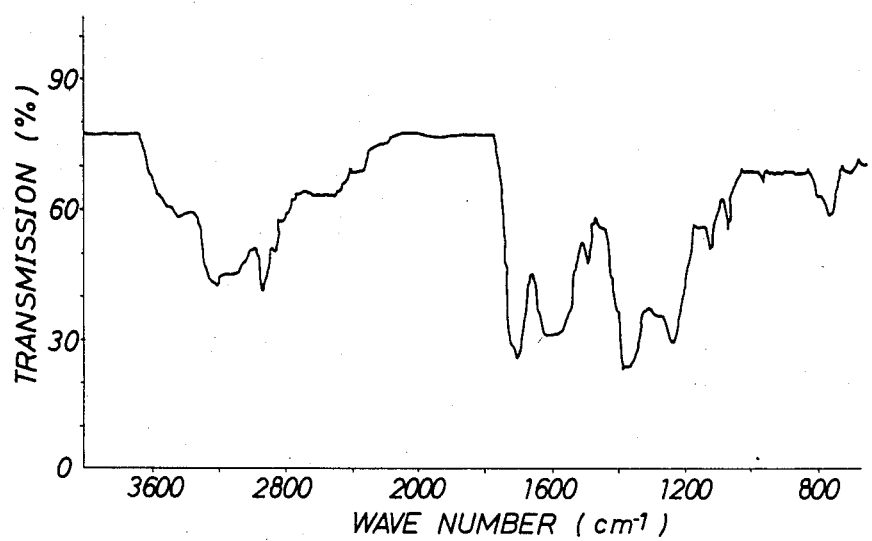
Figure 18:
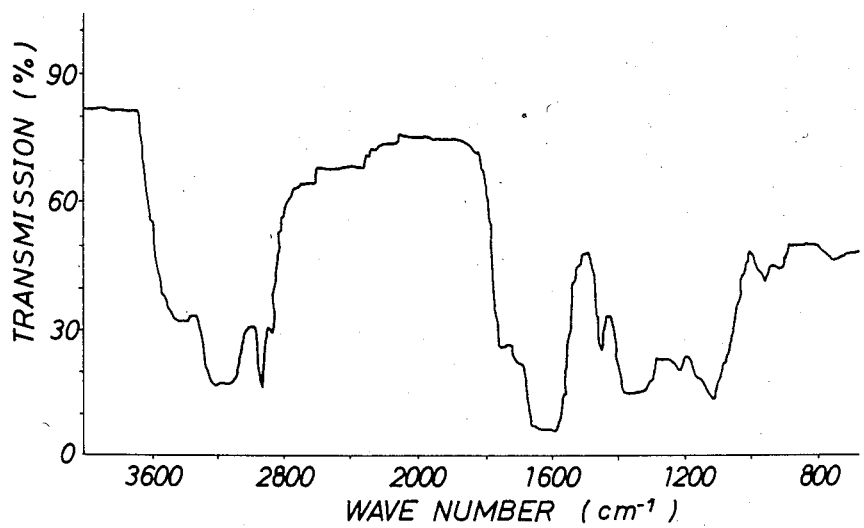
FIG. 18 is the infrared absorption spectrum of the present compound No. 20.

The representative complex compounds of the thus obtained present compounds and the elementary analytical data thereof are shown in Table 1, and the infrared absorption spectra of the representative complex compounds are shown in FIGS. 1 to 18, respectively.

As are seen in the infrared absorption spectra, since in all of the complex compounds of the present invention, the "leaving group" is bonded with Pt via the group,

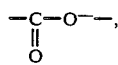

an absorption maximum of

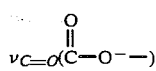

is seen in the vicinity of 1630 cm⁻¹ and an absorption maximum of

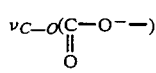

is seen in the vicinity of 1370 cm⁻¹ both in all of the spectra.

In addition, in the infrared absorption spectra of the present compounds having acylated group(s) such as acetylated group as the leaving group, the absorption maximum of $\nu_{C=O}$ in the vicinity of 1750 cm⁻¹ and the absorption maximum of $\nu_{C-O}$ in the vicinity of 1210 cm⁻¹ are seen. Furthermore, except for the strongly hygroscopic complex compounds of the present invention, an absorption maximum of $\nu_{NH_2}$ is seen in the vicinity of 3230 cm⁻¹ in the spectra of the present compounds.

In addition, in the nuclear magnetic resonance absorption spectra(NMR) of the present compounds having acylated group(s) as the leaving group, an absorption of hydrogen of α-carbon is seen at 90.0 ppm together with an absorption of hydrogen of β-carbon atom at 91.2 ppm.

TABLE 1

| No. | Compound of the present invention Name | Found (%) H | Found (%) C | Found (%) N | Calculated (%) H | Calculated (%) C | Calculated (%) N |
|---|---|---|---|---|---|---|---|
| 1 | PtCl(D-glucuronato)(trans-dl-AMCHA).2H₂O | 4.50 | 26.91 | 4.94 | 4.94 | 26.58 | 4.77 |
| 2 | PtCl(D-glucuronato)(cis-dl-AMCHA).H₂O | 4.46 | 27.85 | 4.38 | 4.75 | 27.41 | 4.92 |
| 3 | Pt(tetra-O—acetyl-α-D-glucuronato)₂(trans-dl-AMCHA).3/2H₂O | 5.14 | 39.21 | 2.57 | 4.94 | 39.18 | 2.61 |
| 4 | Pt(tetra-O—acetyl-α-D-glucuronato)₂(cis-dl-AMCHA) | 4.77 | 40.26 | 2.88 | 4.78 | 40.19 | 2.68 |
| 5 | Pt(NO₃)(tetra-O—acetyl-α-D-glucuronato)(trans-dl-AMCHA).2H₂O | 4.43 | 32.36 | 5.11 | 4.73 | 32.26 | 5.37 |
| 6 | Pt(NO₃)(tetra-O—acetyl-α-D-glucuronato)(cis-dl-AMCHA) | 4.48 | 33.16 | 5.71 | 4.22 | 33.78 | 5.68 |
| 7 | Pt(tetra-O—acetyl-β-D-glucuronato)₂(trans-dl-AMCHA) | 4.90 | 39.64 | 2.86 | 4.78 | 40.19 | 2.68 |
| 8 | Pt(tetra-O—acetyl-β-D-glucuronato)₂(cis-dl-AMCHA) | 4.77 | 40.14 | 2.77 | 4.78 | 40.19 | 2.68 |
| 9 | Pt(NO₃)(tetra-O—acetyl-β-D-glucuronato)(trans-dl-AMCHA).2H₂O | 4.33 | 32.06 | 5.40 | 4.73 | 32.23 | 5.37 |
| 10 | Pt(NO₃)(tetra-O—acetyl-β-D-glucuronato)(cis-dl-AMCHA).3/2H₂O | 4.46 | 32.33 | 5.42 | 4.66 | 32.60 | 5.43 |
| 11 | Pt(tetra-O—acetyl-D-gluconato)₂(trans-dl-AMCHA) | 5.36 | 40.45 | 2.80 | 5.15 | 40.04 | 2.67 |
| 12 | Pt(tetra-O—acetyl-D-gluconato)₂(cis-dl-AMCHA) | 5.29 | 39.67 | 2.41 | 5.15 | 40.04 | 2.67 |
| 13 | Pt(NO₃)(tetra-O—acetyl-D-gluconato)(trans-dl-AMCHA) | 4.70 | 33.20 | 5.00 | 4.83 | 32.90 | 5.48 |
| 14 | Pt(NO₃)(tetra-O—acetyl-D-gluconato)(cis-dl-AMCHA) | 4.60 | 32.60 | 5.08 | 4.83 | 32.90 | 5.48 |
| 15 | Pt(penta-O—acetyl-D-gluconato)₂(trans-dl-AMCHA).H₂O | 4.94 | 40.25 | 2.41 | 5.21 | 40.66 | 2.43 |
| 16 | Pt(penta-O—acetyl-D-gluconato)₂(cis-dl-AMCHA).H₂O | 4.90 | 40.06 | 2.53 | 5.21 | 40.66 | 2.43 |
| 17 | Pt(4-carboxyphthalato)(trans-dl-AMCHA).H₂O | 3.83 | 35.13 | 4.87 | 3.64 | 35.00 | 5.10 |
| 18 | Pt(4-carboxyphthalato)(cis-dl-AMCHA).H₂O | 3.72 | 34.85 | 4.93 | 3.64 | 35.00 | 5.10 |
| 19 | Pt(pyruvato)₂(trans-dl-AMCHA).½H₂O | 4.43 | 30.63 | 5.58 | 4.55 | 30.83 | 5.53 |
| 20 | Pt(pyruvato)₂(cis-dl-AMCHA).H₂O | 4.55 | 30.08 | 5.20 | 4.66 | 30.29 | 5.44 |

The antitumour activities of the representatives of the present compounds are shown as follows while describing Test Example thereof.

TEST EXAMPLE

Cells of Leukemia L-1210 were intraperitoneally administered to each of groups of mice (6 animals per group) at a rate of 10⁵ cells per mouse, and while breeding the mice of control group, each of the compounds of the present invention was intraperitoneally administered to each mouse of the test groups after one, five and nine days of the administration of the cells, the mice of the test groups being bred similarly to those of control group. After observing the mortality of all the mice, the mean survival time period after the administration of the cells was obtained in each group including control group.

The ratio of the mean survival time period of each of the test group (T) to the mean survival time period of control group (C) was calculated (T/C) and the result was multiplied by 100 to be shown in the following Table 2 which also shows the dose rates and the number of the mice which were cured after 30 days of the administration of the cells.

| No. of Com-pound | T/C × 100 Item T/C × 100 vs. Amount of administration of | | | | |
|---|---|---|---|---|---|
| | 100 mg/kg | 50 mg/kg | 25 mg/kg | 12.5 mg/kg | 6.25 mg/kg |
| 1 | | | 293 (2) | 118 | 144 |
| 2 | | | 156 | 189 | 271 (2) |
| 4 | 277 (2) | 198 (1) | 145 | | |
| 6 | 120 | 402 (3) | 281 (1) | | |
| 9 | 206 (2) | 253 (1) | | | |
| 10 | 157 | 242 | 204 (1) | | |
| 15 | 103 | 267 | | | |

Note:
The parenthesized figure is the number of mice cured after 30 days of the administration of the cells of Leukemia L-1210.

As will be clearly seen in Table 2, some examples of curing are recognized in the mice administered with the complex compound of the present invention after administration of the cells of Leukemia L-1210, and particularly in the case of administration of Compound No. 10, the rate of life prolongation (T/C×100) was 400% showing the excellent anti-tumour effect of the compound of the present invention.

The mammalian toxicity of the present compounds is low enough to be administered to warm-blooded animals including human.

The process for producing the present compounds will be explained while referring to the following examples.

EXAMPLE 1

Synthesis of [monochloro(D-glucuronato)(trans-dl-AMCHA) platinum(II)], Compound No. 1 of the present invention After dissolving 3.5 g of [Pt(NO$_3$)$_2$(trans-dl-AMCHA)] in 5 ml of water by heating in a flask placed over a fire and cooling the thus prepared solution to room temperature, a solution of 3.36 g (ratio of 2 mols to 1 mol of the above-mentioned complex compound) of sodium D-glucuronate in 21 ml of water was mixed with the thus prepared solution. Thereafter, the mixture was left to react for 3 weeks at room temperature while shielding the light.

After isolating the reaction product by bringing the reaction product into absorption on Sephadex ® G-10 packed in a column of 40 cm in height and 2.6 cm in inner diameter, the thus obtained product was collected by a fraction collector in each specimen of 3 g to be subjected to UV spectrophotometer. The specimen showing a peak at 360 nm were collected, and by freeze-drying the thus collected product, 2.24 g of a solid substance was obtained (yield: 40.5%).

After dissolving 2 g (2.821×10$^{-3}$ mol) of the thus obtained compound in 12 ml of water and dissolving 0.21 g (the same mol as above) of potassium chloride in 3 ml of water, both of the thus prepared solutions were cooled for 3 hours under a cool condition of 5° C. and then mixed together, and the thus obtained mixture was left for 24 hours under the cool condition of 5° C. Then, the precipitated dichloro compound was removed from the mixture by filtration, and the filtrate was subjected to ion-exchange treatment while using about 1 gram of anions and 1 gram of cations. The thus treated filtrate was subjected to adsorption on Sephadex ® G-10 packed in a column of 100 cm in height and 2.6 cm in inner diameter, which had been preliminarily kept under a cool condition of 5° C., and the elution was carried out while using cold water as the eluant in a chromatograph chamber at 5° C. By collecting the thus eluted fractions in each specimen of 4 g, and examining the UV absorption at 290 nm of the thus collected fractional specimens, the elution curve showing two elution bands I and II was graphed. Since the fractions of the elution band II contained an objective compound, the fractions were corrected and collected fraction was subjected to freeze-drying to obtain 0.11 g of Compound No. 1 as a hygroscopic solid substance (yield: 7.1%).

EXAMPLE 2

Synthesis of [monochloro(D-glucuronato)(cis-dl-AMCHA) platinum (II)], Compound No. 2 of the present invention In the same procedures as in Example 1 except for using [Pt(NO$_3$)$_2$(cis-dl-AMCHA)] instead of [Pt(NO$_3$)$_2$(trans-dl-AMCHA)] in Example 1, Compound No. 2 was obtained as a hygroscopic solid compound in an amount of 0.19 g (yield: 12.3%).

EXAMPLE 3

Synthesis of [bis(tetra-O-acetyl-α-D-glucuronato)(trans-dl-AMCHA) platinum(II)], Compound No. 3 of the present invention After dissolving 0.5 g (1.119×10$^{-3}$ mol) of [Pt(NO$_3$)$_2$-(trans-dl-AMCHA)] in 10 ml of water by heating in a flask placed on a fire, and cooling the thus prepared solution to room temperature, a solution of 0.81 g (ratio of 2 mols to 1 mol of the above-mentioned complex compound, 2.237×10$^{-3}$ mol) of tetra-O-acetyl-α-D-glucuronic acid in 50 ml of ethanol was mixed with the aqueous solution.

After adding 1.34 ml (2.237×10$^{-3}$ mol) of an aqueous solution of sodium hydroxide of a concentration of 1 g/15 ml of water to the thus prepared mixture, the newly prepared mixture was left to react for 3 days at room temperature while shielding the light. Then, the reaction mixture was dried up to be solid under a reduced pressure, and the solid residue was extracted three times with each 20 ml of benzene. By drying up the thus obtained extract, 0.31 g of Compound No. 3 was obtained as a solid substance (yield: 26.5%).

EXAMPLE 4

Synthesis of [bis(tetra-O-acetyl-α-D-glucuronato)(cis-dl-AMCHA) platinum(II)], Compound No. 4 of the present invention In the same procedures as in Example 3 except for using [Pt(NO$_3$)$_2$(cis-dl-AMCHA)] instead of [Pt(NO$_3$)$_2$(trans-dl-AMCHA)] in Example 3, Compound No. 4 was obtained in an amount of 0.36 g (yield: 30.8%).

EXAMPLE 5

Synthesis of
[bis(tetra-O-acetyl-β-D-glucuronato)(trans-dl-AMCHA) platinum(II)], Compound No. 7 of the present invention In the same procedures as in Example 3 except for using tetra-O-acetyl-β-D-glucuronic acid instead of tetra-O-acetyl-α-D-glucuronic acid in Example 3, 0.40 g of Compound No. 7 was obtained (yield: 34.2%).

EXAMPLE 6

Synthesis of
[bis(tetra-O-acetyl-β-D-glucuronato)(cis-dl-AMCHA) platinum(II)], Compound No. 8 of the present invention In the same procedures as in Example 4 except for using tetra-O-acetyl-β-D-glucuronic acid instead of tetra-O-acetyl-α-D-glucuronic acid in Example 4, 0.34 g of Compound No. 8 was obtained (yield: 29.1%).

EXAMPLE 7

Synthesis of
[(tetra-O-acetyl-α-D-glucuronato)(trans-dl-AMCHA)-platinum(II) nitrate], Compound No. 5 of the present invention.

After dissolving 0.5 g ($1.119 \times 10^{-3}$ mol) of [Pt(NO$_3$)$_2$- (trans-dl-AMCHA)] in 10 ml of water by heating in a flask placed directly over a fire, and cooling the thus prepared solution to room temperature, a solution of 0.40 g (equimolar to the above-mentioned complex compound, $1.119 \times 10^{-3}$ mol) of tetra-O-acetyl-α-D-glucuronic acid in 25 ml of ethanol was mixed with the aqueous solution, and after adding 0.67 ml ($1.119 \times 10^{-3}$ mol) of a solution of sodium hydroxide at a concentration of 1 g of NaOH in 15 ml of water (equimolar to the above-mentioned complex compound) into the thus prepared mixture, the thus prepared mixture was left to react for 3 days at room temperature while shielding the light. Then, the reaction mixture was dried up to a solid matter at 40° to 50° C. under a reduced pressure, and the thus obtained solid residue was washed 2 times with each 30 ml of benzene, and the thus washed solid residue was extracted two times with each 20 ml of chloroform. By drying up the extract under a reduced pressure, 0.09 g of Compound No. 5 was obtained as a solid substance (yield: 10.8%).

EXAMPLE 8

Synthesis of
[(tetra-O-acetyl-α-D-glucuronato)(cis-dl-AMCHA) platinum(II) nitrate], Compound No. 6 of the present invention In the same procedures as in Example 7 except for using [Pt(NO$_3$)$_2$(cis-dl-AMCHA)] instead of [Pt(NO$_3$)$_2$(trans-dl-AMCHA)] in Example 7, 0.12 g of Compound No. 6 was obtained (yield: 14.5%).

EXAMPLE 9

Synthesis of
[(tetra-O-acetyl-β-D-glucuronato)(trans-dl-AMCHA) platinum(II) nitrate], Compound No. 9 of the present invention In the same procedures as in Example 7 except for using tetra-O-acetyl-β-D-glucuronic acid instead of tetra-O-acetyl-α-D-glucuronic acid in Example 7, 0.14 g of Compound No. 9 was obtained (yield: 16.9%).

EXAMPLE 10

Synthesis of
[(tetra-O-acetyl-β-D-glucuronato)(cis-dl-AMCHA) platinum(II) nitrate], Compound No. 10 of the present invention In the same procedures as in Example 8 except for using tetra-O-acetyl-β-D-glucuronic acid instead of tetra-O-acetyl-α-D-glucuronic acid in Example 8, 0.16 g of Compound No. 10 was obtained (yield: 19.3%).

EXAMPLE 11

Synthesis of
[bis(2,3,4,6-tetra-O-acetyl-D-gluconato)(trans-dl-AMCHA) platinum(II)], Compound No. 11 of the present invention In the same procedures as in Example 3 except for using 2,3,4,6-tetra-O-acetyl-D-gluconic acid instead of tetra-O-acetyl-α-D-glucuronic acid in Example 3, 0.41 g of Compound No. 11 was obtained (yield: 35.0%).

EXAMPLE 12

Synthesis of
[bis(2,3,4,6-tetra-O-acetyl-D-gluconato)(cis-dl-AMCHA) platinum(II)], Compound No. 12 of the present invention In the same procedures as in Example 11 except for using [Pt(NO$_3$)$_2$(cis-dl-AMCHA)] instead of [Pt(NO$_3$)$_2$(trans-dl-AMCHA)] in Example 11, 0.34 g of Compound No. 12 was obtained (yield: 29.1%).

EXAMPLE 13

Synthesis of
[(2,3,4,6-tetra-O-acetyl-D-gluconato)(trans-dl-AMCHA) platinum (II) nitrate], Compound No. 13 of the present invention In the same procedures as in Example 7 except for using (2,3,4,6-tetra-O-acetyl-D-gluconic acid) instead of tetra-O-acetyl-α-D-glucuronic acid in Example 7, 0.25 g of Compound No. 13 was obtained (yield: 30.1%).

EXAMPLE 14

Synthesis of
[(2,3,4,6-tetra-O-acetyl-D-gluconato)(cis-dl-AMCHA) platinum(II) nitrate], Compound No. 14 of the present invention In the same procedures as in Example 13 except for using [Pt(NO$_3$)$_2$(cis-dl-AMCHA)] instead of [Pt(NO$_3$)$_2$(trans-dl-AMCHA)] in Example 13, 0.30 g of Compound No. 14 was obtained (yield: 36.1%).

EXAMPLE 15

Synthesis of
[bis(penta-O-acetyl-D-gluconato)(trans-dl-AMCHA) platinum (II)], Compound No. 15 of the present invention In the same procedures as in Example 3 except for using penta-O-acetyl-D-gluconic acid instead of tetra-O-acetyl-α-D-glucuronic acid in Example 3, 0.42 g of Compound No. 15 was obtained (yield: 33.3%).

EXAMPLE 16

Synthesis of [bis(penta-O-acetyl-D-gluconato)(cis-dl-AMCHA) platinum(II)], Compound No. 16 of the present invention In the same procedures as in Example 15 except for using [Pt(NO$_3$)$_2$(cis-dl-AMCHA)] instead of [Pt(NO$_3$)$_2$(trans-dl-AMCHA)] in Example 15, 0.46 g of Compound No. 16 was obtained (yield: 36.0%).

EXAMPLE 17

Synthesis of [(4-carboxyphthalato)(cis-dl-AMCHA) platinum(II)], Compound No. 18 of the present invention After dissolving 0.5 g ($1.119 \times 10^{-3}$ mol) of [Pt(NO$_3$)$_2$(cis-dl-AMCHA)] in 5 ml of water by heating in a flask placed directly over a fire, and cooling the thus prepared solution to room temperature, a solution of 0.23 g (equimolar to the above-mentioned complex compound, $1.119 \times 10^{-3}$ mol) of 4-carboxyphthalic acid in 3 ml of water was mixed with the thus prepared solution, and after stirring the mixture for 24 hours, the pH of the mixture was adjusted to 2 to 3. The thus formed precipitate was collected by filtration and dried to obtain 0.05 g of Compound No. 18 (yield: 8%).

EXAMPLE 18

Synthesis of [4-carboxyphthalato(trans-dl-AMCHA) platinum(II)], Compound No. 17 of the present invention In the same procedures as in Example 17 except for using [Pt(NO$_3$)$_2$(trans-dl-AMCHA)] instead of [Pt(NO$_3$)$_2$(cis-dl-AMCHA)] in Example 17, 0.05 g of Compound No. 17 was obtained (yield: 8%).

EXAMPLE 19

Synthesis of [bis(pyruvato)(cis-dl-AMCHA) platinum(II)], Compound No. 20 of the present invention A solution obtained by dissolving 1.0 g ($2.387 \times 10^{-3}$ mol) of [Pt(H$_2$O)(SO$_4$)(cis-dl-AMCHA)] in 20 ml of water under heating was left to cool to room temperature, and a solution of 0.74 g (equimolar to the above-mentioned complex compound, $2.380 \times 10^{-3}$ mol) of barium pyruvate in 10 ml of water was added to the thus cooled solution little by little. The thus precipitated-barium sulfate was removed by filtration, and the filtrate was dried up at 40° to 50° C. under a reduced pressure. The thus obtained solid residue was dissolved in 2-3 ml of water, and after filtering the solution, 10 times by volume of acetone were added to the filtrate. The thus formed precipitate was collected by filtration and dried up to obtain 0.32 g of Compound No. 20 (yield: 26.9%).

EXAMPLE 20

Synthesis of [bis(pyruvato)(trans-dl-AMCHA) platinum(II)], Compound No. 19 of the present invention In the same procedures as in Example 19 except for using [Pt(H$_2$O))(SO$_4$) (trans-dl-AMCHA)] instead of [Pt(H$_2$O)(SO$_4$)(cis-dl-AMCHA)] in Example 19, 0.52 g of Compound No. 19 was obtained (yield: 44.0%).

REFERENCE EXAMPLE 1

Synthesis of tetra-O-acetyl-α-(and β)-D-glucuronic acid

While keeping a solution of 79.83 g of p-toluene-sulfonic acid hydrate in 282.4 ml of acetic anhydride at a temperature of lower than 3° C. under agitation, crystals of sodium salt of glucuronolactone which had been obtained by adding 46.69 g of sodium hydrogencarbonate(0.555 mol) into an aqueous solution of 92.32 g (0.525 mol) of D-glucuronolactone were added to the thus prepared solution little by little.

After adding 565 ml of ether and 14.26 g of sodium acetate trihydrate into the thus prepared aqueous mixture, the ether layer was removed, and the aqueous layer was extracted with 200 ml of chloroform. After distilling ether and chloroform off from the extract, respectively under a reduced pressure, the thus obtained oily material was left in a draft chamber, and after removing acetic acid therefrom, water was added to the residue to effect crystallization of the residue, thereby obtaining 23.16 g of tetra-O-acetyl-D-glucopyranuronic acid. The separation of the anomers was carried out while utilizing the difference of the solubility between the pyridine salts of the two anomers in ether.

Namely, 23.16 g of the thus obtained tetra-O-acetyl-D-glucopyranuronic acid was dissolved in 24 ml of pyridine, and ether was added to the thus prepared solution, and the thus formed white precipitate was collected by filtration. Thus, 13.47 g of pyridine salt of β-anomer were obtained.

Further, by distilling the solvent in the resultant filtrate under a reduced pressure, pyridine salt of α-anomer was obtained as an oily material.

Each of the thus obtained anomers was dissolved in water, and 35% hydrochloric acid was added to the aqueous solution to obtain crystals as the precipitate. By recrystallizing the two kinds of the thus precipitated crystals, respectively from ethanol, 5.49 g of tetra-O-acetyl-α-D-glucuronic acid and 9.55 g of tetra-O-acetyl-β-D-glucuronic acid were obtained.

PREFERENCE EXAMPLE 2

Synthesis of 2,3,4,6-tetra-O-acetyl-D-gluconic acid

Into a solution of 20 g of ZnCl$_2$ in 250 ml of acetic anhydride, 50 g (0.281 mol) of D-glucono-δ-lactone were added, and the mixture was stirred for one night while cooling thereof so as to maintain the mixture at a temperature of not higher than 50° C. Thereafter, 1 liter of water was added to the reaction mixture, and the thus formed precipitate was collected by filtration and recrystallized from ethanol to obtain 85 g of 2,3,4,6-tetra-O-acetyl-D-gluconic acid.

REFERENCE EXAMPLE 3

Synthesis of 2,3,4,5,6-penta-O-acetyl-D-gluconic acid 15 g of 2,3,4,6-tetra-O-acetyl-D-gluconic acid obtained in Reference Example 2 was slowly added to a solution of 5.4 g of ZnCl$_2$ in 57 ml of acetic anhydride at a temperature of from 0° to 10° C. After leaving the reaction mixture for one night, 300 ml of water were added to the reaction mixture, and the aqueous mixture was extracted 4 times with each 30 ml of chloroform.

After condensing the extract, 75 ml of toluene were added to the condensate and the mixture was further condensed. Ethanol was added to the condensate to precipitate crystals therefrom, and the crystals were recrystallized from ethanol to obtain 45 g of 2,3,4,5,6-penta-O-acetyl-D-gluconic acid.

What is claimed is:

1. Complex compounds represented by the formula(I):

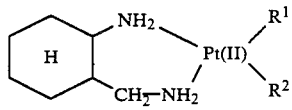
(I)

wherein one of $R^1$ and $R^2$ represents a group selected from the group consisting of (1) glucuronato groups whose hydroxyl groups may be acylated, (2) gluconato groups whose hydroxyl groups may be acylated, (3) pyruvato group and (4) nitrato group, and the other of $R^1$ and $R^2$ represents a group selected from the group consisting of (i) glucuronato groups whose hydroxyl groups may be acylated, (ii) gluconato groups whose hydroxyl groups may be acylated, (iii) pyruvato group and (iv) halogen atoms, or $R^1$ and $R^2$ represent together the group represented by the formula (II):

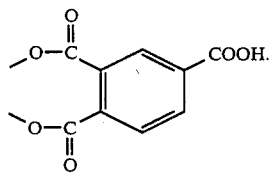
(II)

2. Complex compounds according to claim 1, wherein $R^1$ represents a glucuronato group, a tetra-O-acylglucuronato group or a nitrato group and $R^2$ represents a chlorine atom or a tetra-O-acetylglucuronato group, or $R^1$ and $R^2$ represent together the group represented by the formula(II).

3. PtCl(D-glucuronato)(cis- or trans-dl-2-aminomethylcyclohexylamine).

4. Pt(tetra-O-acetyl-α-D-glucuronato)$_2$(cis-dl-2-aminomethylcyclohexylamine).

5. Pt(NO$_3$)(tetra-O-acetyl-α-D-glucuronato)(cis-dl-2-aminomethylcyclohexylamine).

6. Pt(NO$_3$)(tetra-O-acetyl-β-D-glucuronato)(cis- or trans-dl-2-aminomethylcyclohexylamine).

7. Pt(4-carboxyphthalato)(trans-dl-2-aminomethylcyclohexylamine).

* * * * *